(12) United States Patent
Jamruszka-Lewis

(10) Patent No.: US 7,950,183 B2
(45) Date of Patent: May 31, 2011

(54) METHODS OF PRODUCING A SYNCHRONIZED POPULATION OF CONIFER SOMATIC EMBRYO GERMINANTS

(75) Inventor: Amy M. Jamruszka-Lewis, Sumner, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 347 days.

(21) Appl. No.: 12/103,370

(22) Filed: Apr. 15, 2008

(65) Prior Publication Data
US 2008/0206868 A1    Aug. 28, 2008

Related U.S. Application Data

(62) Division of application No. 11/566,123, filed on Dec. 1, 2006, now Pat. No. 7,685,769.

(60) Provisional application No. 60/753,453, filed on Dec. 22, 2005.

(51) Int. Cl.
C12N 5/04       (2006.01)
A01H 7/00       (2006.01)
A01G 1/00       (2006.01)
A01C 1/06       (2006.01)

(52) U.S. Cl. ...... 47/58.1; 435/420; 435/422; 435/430.1; 47/57.6

(58) Field of Classification Search ......................... None
See application file for complete search history.

(56) References Cited

U.S. PATENT DOCUMENTS

| | | |
|---|---|---|
| 4,217,730 A | 8/1980 | Abo El-Nil |
| 4,801,545 A | 1/1989 | Stuart et al. |
| 4,957,866 A | 9/1990 | Gupta et al. |
| 5,034,326 A | 7/1991 | Pullman et al. |
| 5,036,007 A | 7/1991 | Gupta et al. |
| 5,041,382 A | 8/1991 | Gupta et al. |
| 5,183,757 A | 2/1993 | Roberts |
| 5,187,092 A | 2/1993 | Uddin |
| 5,236,841 A | 8/1993 | Gupta et al. |
| 5,238,835 A | 8/1993 | McKersie et al. |
| 5,294,549 A | 3/1994 | Pullman et al. |
| 5,413,930 A | 5/1995 | Becwar et al. |
| 5,464,769 A | 11/1995 | Attree et al. |
| 5,482,857 A | 1/1996 | Gupta et al. |
| 5,491,090 A | 2/1996 | Handley, III et al. |
| 5,501,972 A | 3/1996 | Westcott |
| 5,506,136 A | 4/1996 | Becwar et al. |
| 5,523,230 A | 6/1996 | Smith |
| 5,534,433 A | 7/1996 | Coke |
| 5,534,434 A | 7/1996 | Coke |
| 5,563,061 A | 10/1996 | Gupta |
| 5,564,224 A | 10/1996 | Carlson et al. |
| 5,565,355 A | 10/1996 | Smith |
| 5,587,312 A | 12/1996 | van Holst et al. |
| 5,610,051 A | 3/1997 | Becwar et al. |
| 5,677,185 A | 10/1997 | Handley, III |
| 5,731,191 A | 3/1998 | Rutter et al. |
| 5,731,203 A | 3/1998 | Handley, III |
| 5,731,204 A | 3/1998 | Rutter et al. |
| 5,821,126 A | 10/1998 | Durzan et al. |
| 5,840,581 A | 11/1998 | Carraway et al. |
| 5,850,032 A | 12/1998 | Wann |
| 5,856,191 A | 1/1999 | Handley, III |
| 5,985,667 A | 11/1999 | Attree et al. |
| 6,022,744 A | 2/2000 | Tetteroo et al. |
| 6,117,678 A | 9/2000 | Carpenter et al. |
| 6,134,830 A * | 10/2000 | Welty ........................ 47/58.1 R |
| 6,150,167 A | 11/2000 | Carpenter et al. |
| 6,180,405 B1 | 1/2001 | Aitken-Christie et al. |
| 6,200,809 B1 | 3/2001 | Klimaszewska et al. |
| 6,340,594 B1 | 1/2002 | Attree et al. |
| 6,372,496 B1 | 4/2002 | Attree et al. |
| 6,417,001 B2 | 7/2002 | Aitken-Christie et al. |
| 6,444,467 B1 | 9/2002 | Fan et al. |
| 6,492,174 B1 | 12/2002 | Pullman et al. |

(Continued)

FOREIGN PATENT DOCUMENTS

EP            0 300 730 B1      1/1989

(Continued)

OTHER PUBLICATIONS

Hansen et al. "Recent advances in the transformation of plants," Trends in Plant Science Reviews, Jun. 1999, vol. 4, No. 6, pp. 226-231.*

Attree, S.M. et al., "Somatic Embryo Maturation, Germination, and Soil Establishment of Plants of Black and White Spruce (*Picea mariana* and *Picea glauca*)," Can. J. Bot. 68:2583-2589, 1990.

Attree, S.M., et al., "Initiation of Embryogenic Callus and Suspension Cultures, and Improved Embryo Regeneration of Protoplasts, of White Spruce (*Picea glauca*)," Can. J. Bot. 67:1790-1795, 1989.

Attree, S.M., et al., "Plantlet Regeneration From Embryogenic Protoplasts of White Spruce (*Picea glauca*)," Bio/Technology 7:1060-1062, 1989.

(Continued)

*Primary Examiner* — Annette H Para
(74) *Attorney, Agent, or Firm* — Christensen, O'Connor Johnson Kindness PLLC

(57) ABSTRACT

In one aspect, the present invention provides methods of producing a synchronized population of conifer somatic embryo germinants in preparation for transplantation. The methods of the invention comprise the steps of: (a) culturing conifer somatic embryos on sterile germination medium for a sufficient period of time to produce germinants comprising a visible, well-defined epicotyl stem of a desired length; (b) selecting a plurality of germinants having an epicotyl stem of the desired length; (c) storing the selected germinants having an epicotyl stem of the desired length produced in step (a) while still on the sterile germination medium from step (a) in a cold environment in which the temperature is in the range of 0.5° C. to 10° C. for a time period up to six months; and (d) transferring the germinants stored according to step (c) from the germination medium into water for a time of up to about four weeks at a temperature of about 0.5° C. to about 5° C. prior to planting the selected germinants into growth medium.

10 Claims, No Drawings

U.S. PATENT DOCUMENTS

| | | | |
|---|---|---|---|
| 2002/0012994 A1 | 1/2002 | Aitken-Christie et al. | |
| 2002/0092037 A1 | 7/2002 | Connett-Porceddu et al. | |
| 2002/0100083 A1 | 7/2002 | Connett-Porceddu et al. | |
| 2003/0182696 A1* | 9/2003 | Ramirez Serrano | 800/319 |

FOREIGN PATENT DOCUMENTS

| | | |
|---|---|---|
| EP | 0 618 766 B1 | 10/1994 |
| EP | 0 934 691 A2 | 8/1999 |
| WO | WO 95/33822 A1 | 12/1995 |
| WO | WO 98/48279 A1 | 10/1998 |
| WO | WO 99/46977 | 9/1999 |
| WO | WO 01/20972 A1 | 3/2001 |

OTHER PUBLICATIONS

Boulay, M.P., et al., "Development of Somatic Embryos From Cell Suspension Cultures of Norway Spruce (*Picea abies* Karst.)," Plant Cell Reports 7:134-137, 1988.

Cornu, D. and C. Geoffrion, "Aspects of Somatic Embryogenesis in Larch Trees," *Bull. Soc. Bot. Fr.*, 137 Actual. Bot. (3/4):25-34, 1990 [translation].

Garin E et al, "Effects of sugars, amino acids, and culture technique on maturation of somatic embryos of Pinus strobes on medium with two gellan gum concentrations," *Plant Cell Tiss & Org Cult* (62) 27-27, 2000.

Gupta, P.K., et al., "Scale-Up Somatic Embryogenesis of Conifers For Reforestation," Proceedings of the 3rd Canadian Workshop on Plant Tissue Culture and Genetic Engineering, University of Guelph, Symposium 1: Somatic Embryogenesis and Synthetic Seeds, Abstract, Jun. 1992.

Gupta PK et al, "Liquid media and automation strategy for large-scale production of conifer somatic embryos for reforestation," *In vitro cell & devel bio-Animal* 1999, 35: Abstract W-32.

Gupta PK et al, "Somatic embryo development in liquid medium for large-scale propagation of conifer trees," *2003 Congress on In Vitro Biol* May 31-Jun. 4, 2003; program abstracts p. 14A, Abstract P-28.

Hakman, I. and L.C. Fowke, "An Embryogenic Cell Suspension Culture of *Picea glauca* (White Spruce)," *Plant Cell Reports* 6:20-22, 1987.

Hormaza JI, "Early selection in cherry combining RAPDs with embryo culture," *Sci Horti* 79 pp. 121-126 (1990).

Jain, S.M., et al., Forestry Sciences: Somatic Embryogenesis in Woody Plants, vol. 3, Gymnosperms, Kluwer Academic Publishers, Netherlands, 1995.

Keinonen-Mettälä, K., et al., "Somatic Embryogenesis of *Pinus sylvestris*," Scand. J. For. Res. 11:242-250, 1996.

Klimaszewska K et al, "Maturation of somatic embryos of pinus strobes is promoted by a high concentration of gellan gum," *Physiologica Plantarum* (100) 949-957, 1997.

Krogstrup, P. "Somatic Embryogenesis in Sitka Spruce (*Picea sitchensis* (Bong.) Carr.)," *Plant Cell Reports* 7:594-597, 1988.

Lelu Ma et al, "Somatic embryogenesis and plantlet development in *Pinus sylvestris* and pinus pinaster on median with and without growth regulators," *Phys Plantarum, Munksgaard Intl* (105) 719-718, 1999.

Lelu, M.A. et al., "Effect of Maturation Duration on Desiccation Tolerance in Hybrid Larch (*Larix X leptoeuropaea dengler*) Somatic Embryos," *In Vitro Cell. Dev. Biol.* 3115-20, 1995.

Lu, C.-Y. and T.A. Thorpe, "Somatic Embryogenesis and Plantlet Regeneration in Cultured Immature Embryos of *Picea glauca*," *J. Plant Physiol.* 128:297-302, 1987.

Mathur, G. et al., "Studies on Somatic Embryogenesis From Immature Zygotic Embryos of CHIR Pine (*Pinus roxburghii* Sarg.)," Current Science 79(7):999-1004, 2000.

Norgaard, J.V., and P. Krogstrup, "Cytokinin Induced Somatic Embryogenesis From Immature Embryos of *Abies nordmanniana* Lk.," *Plant Cell Reports* 9:509-513, 1991.

Pullman GS et al., "Improving loblolly pine somatic embryo maturation: comparisons of somatic and zygotic embryo morphology, germination and gene expression," *Plant Cell Rep* 21 (2003) 747-758.

Ramarosandtradana LH et al, "Effects of Carbohydrate Source, Polyethylene Glycol and Gellan Gum Concentration on Embryonal-Suspensor Mass (ESM) Proliferation and Maturation of Maritime Pine Somatic Embryos," *In vitro Cellular and Developmental Biology-Plant* 37:29-34.

Roberts, D.R., "Abscisic Acid and Mannitol Promote Early Development, Maturation and Storage Protein Accumulation in Somatic Embryos of Interior Spruce," *Physiologia Plantarum* 83:247-254, 1991.

Roberts, D.R et al., "Interaction Between Maturation and High Relative Humidity Treatments and Their Effects on Germination of Sitka Spruce Somatic Embryos," *J. Plant Physiol.* 138:1-6, 1991.

Roberts, D.R., et al., "Synchronous and High Frequency Germination of Interior Spruce Somatic Embryos Following Partial Drying at High Relative Humidity," *Can. J. Bot.* 68:1086-1090, 1989.

Saar A et al., "Gametophilic competition in pearl millet, Penniseum typhoides (Staph et. Hubb.)," *Genome* 30: pp. 924-929 (1988).

Taber RP et al., "Kinetics of Douglas-fir (*Pseudotsungo menziesii*) somatic embryo development," *Can J Bot* (76): 838-871, 1998.

Thompson, R.G. and P. von Aderkas, "Somatic Embryogenesis and Plant Regeneration From Mature Embryos of Western Larch," *Plant Cell Reports* 11:379-386, 1992.

Timmis, R., "Bioprocessing for Tree Production in the Forest Industry: Conifer Somatic Embryogenesis," Biotechnol. Prog. 14(1):156-166, 1998.

Von Aderkas, P., et al., "Charcoal Affects Early Development and Hormonal Concentrations of Somatic Embryos of Hybrid Larch," Tree Physiology 22:431-434, 2002.

Von Arnold, S. and I. Hakman, "Regulation of Somatic Embryo Development in *Picea abies* by Abscisic Acid (ABA)," *J. Plant Physiol.* 132:164-169, 1988.

Von Arnold, S. and T. Eriksson, "A Revised Medium for Growth of Pea Mesophyll Protoplasts," *Physiol. Plant* 39:257-260, 1977.

Webb, D.T., et al., "Factors Influencing the Induction of Embryogenic and Caulogenic Callus From Embros of *Picea glauca* and *P. engelmanii*," Can. J. For. Res. 19:1303-1308, 1989.

Chandel, K.P.S., and R. Pandey, "Plant Genetic Resources Conservation: Recent Approaches," in R.S. Paroda et al. (eds.), "Plant Genetic Resources, Conservation and Management, Concepts and Approaches," Malhotra Publishing House, New Delhi, India, 1991, pp. 247-263.

\* cited by examiner

METHODS OF PRODUCING A SYNCHRONIZED POPULATION OF CONIFER SOMATIC EMBRYO GERMINANTS

CROSS REFERENCE TO RELATED APPLICATION

The present application is a divisional of pending U.S. patent application Ser. No. 11/566,123, filed Dec. 1, 2006, which claims the benefit of U.S. Provisional Application No. 60/753,453, filed Dec. 22, 2005.

FIELD OF THE INVENTION

The present invention relates to methods for storing conifer somatic embryo germinants.

BACKGROUND OF THE INVENTION

The demand for coniferous trees, such as pines and firs, to make wood products continues to increase. One proposed solution to meeting this high demand is to identify individual trees that possess desirable characteristics, such as a rapid rate of growth, and produce numerous, genetically identical, clones of the superior trees by somatic cloning.

Somatic cloning is the process of producing plant embryos, in vitro, from plant cells that are not zygotes. These clones can be cultivated to yield stands, or whole forests, of conifer trees that possess the desirable characteristic(s). One method for somatically cloning trees utilizes in vitro treatment of isolated, living, conifer tissue under conditions that promote formation of conifer somatic embryos, and then whole plants from the treated tissue. An explant such as an immature seed or the embryo from an immature seed is placed on a gelled initiation medium. This medium will usually contain plant growth hormones from the groups known as auxins and cytokinins. If initiation is successful a gelatinous mass containing multiple immature embryos will be generated in several weeks. This mass is then removed and subcultured on a maintenance and multiplication medium which may be gelled, liquid, or some combination of these. Embryos from maintenance medium may then be placed on a development medium that normally lacks the auxins and cytokinins but may instead include the hormone abscisic acid. The somatic embryos develop into cotyledonary embryos with a size and morphology that closely resembles their mature zygotic counterparts. The embryos are then placed on a germination medium on which radicle and epicotyl elongation occur over a period of several weeks. The germinants are then removed and placed in soil for further development into plantlets. After a period of greenhouse growth they may be outplanted. Alternatively, the embryos removed from the development medium may be placed into manufactured seeds; e.g., as shown in Carlson et al., U.S. Pat. No. 5,236,469.

A continuing problem, however, has been that conversion percentage from somatic embryos to plants growing in soil has frequently been lower than desired. In addition, a logistical problem exists for handling large numbers of conifer somatic embryos that are not packaged into manufactured seeds. These embryos are individually removed from the sterile development medium and placed on a germination medium. After an appropriate time the germinants are placed in a potting soil mixture for further growth. Typically many hundreds of thousands of germinants are potted at once in clonal field tests. The germinants are very tender and susceptible to damage by disease organisms such as fungi. In addition, it is preferable to outplant germinants that have similar dimensions in clonal field tests in order to obtain reliable results regarding the characteristics of various clones. However, a logistical challenge exists for producing a population of germinants having similar dimensions at the time of outplanting.

There is therefore a continuing need for a method for storing conifer germinants that reduces the risk of contamination with microbes, is amenable to large scale production, and results in a high conversion rate after transplantation.

SUMMARY OF THE INVENTION

In one aspect, the present invention provides methods of storing conifer somatic embryo germinants germinated on a sterile germination medium for delayed transplanting into a growth medium. The methods of the invention comprise the steps of: (a) placing the germinants while still on sterile germination medium into a cold environment in which the temperature is in the range of 0(0.5° C. to 10° C. for a time period up to 6 months, said germinants comprising a visible, well-defined epicotyl and radicle; and (b) placing the germinants in water for a time greater than about 1 hour at a temperature below about 24° C. prior to transplantation into growth medium.

In another aspect, the present invention provides methods of producing and storing germinants prior to transplantation into growth medium. The methods of this aspect of the invention comprise the steps of: (a) culturing conifer somatic embryos on sterile germination medium for a sufficient period of time to produce germinants, said germinants comprising a visible, well-defined epicotyl and radicle; (b) placing the germinants while still on sterile germination medium into a cold environment in which the temperature is in the range of 0.5° C. to 10° C. for a time period up to 6 months, and (c) placing the germinants in water at a temperature below about 24° C. for a time greater than about 1 hour prior to transplanting the stored germinants into growth medium.

In another aspect, the present invention provides methods of increasing the conversion percentage from somatic embryos to plants growing in growth medium. In accordance with this aspect of the invention the methods comprise the steps of: (a) culturing conifer somatic embryos on sterile germination medium for a sufficient period of time to produce germinants, said germinants comprising a visible, well-defined epicotyl and radicle; (b) placing the germinants while still on sterile germination medium into a cold environment in which the temperature is in the range of 0.5° C. to 10° C. for a time period up to 6 months; (c) placing the germinants in water for a time greater than about 1 hour at a temperature below about 24° C.; and (d) removing the germinants from the water and transplanting them into growth medium for further growth.

In yet another aspect, the present invention provides methods of producing a synchronized population of somatic embryo germinants in preparation for transplantation. In accordance with this aspect of the invention the methods comprise the steps of: (a) culturing somatic embryos on sterile germination medium for a sufficient period of time to produce germinants having a desired dimension; (b) selecting a plurality of germinants having the desired dimension; (c) storing the selected germinants while still on sterile germination medium in a cold environment in which the temperature is in the range of 0.5° C. to 10° C. for a time period up to 6 months; and (d) placing the stored germinants in water for a time greater than about 1 hour at a temperature below about 24° C. prior to planting the selected germinants into growth medium.

DETAILED DESCRIPTION OF THE PREFERRED EMBODIMENT

The following examples merely illustrate the best mode now contemplated for practicing the invention, but should not be construed to limit the invention.

As used herein, the term "cotyledonary embryo" means an embryo that possesses one or more cotyledons.

As used herein, the term "somatic embryo" refers to a plant embryo that developed in vitro from a plant cell, or tissue, that is not a zygote.

As used herein, the term "embryogenic tissue" refers to any tissue, derived from a conifer which is capable of producing one or more conifer cotyledonary somatic embryos, including, for example, conifer embryonal suspensor masses.

As used herein the term "germinant" refers to an immature plant that possesses a well developed radicle and cotyledonary structure with a growing epicotyl, both readily apparent to the naked eye, and ready for planting in soil. For example, the germinants typically have an epicotyl of about 10 mm or greater.

As used herein, the term "converted embryo" is an embryo that has germinated and been established as a plant growing in soil.

As used herein, the term "synchronized population of germinants" refers to a stock of germinants having a target specification at outplanting. The germinants may be cultured to a desired target specification, such as having a desired dimension, (e.g., an epicotyl stein length of at least 10 mm).

Unless stated otherwise, all concentration values that are expressed as percentages are weight per volume percentages.

The present invention provides methods for storing conifer somatic embryo germinants. The methods each include the step of placing the germinants while still on germination medium into a cold environment for a time period of up to 6 months (such as, for example, from at least 2 weeks to 24 weeks, or such as from 4 weeks to 10 weeks), followed by the step of placing the germinants in water for a time greater than about 1 hour up to from one to several weeks (such as, for example from several hours up to one week) prior to transplantation into a growth medium. It has been observed that conifer germinants may be stored up to 4 weeks or more prior to planting in growth medium when stored according to the methods of the invention without loss of post-transplant vigor.

The storage methods of the invention are particularly advantageous in that they make it possible to produce a synchronized population of germinants in preparation for transplantation. The synchronized population of germinants are produced by culturing germinants to a desired target specification, and storing the germinants in a cold environment on sterile germination medium as they become available over a period of days or weeks. The stored germinants are then placed into water for a time greater than about 1 hour at a temperature below about 24° C. prior to planting. Consequently, the storage methods of the invention allow for a longer embryo production window (e.g. several weeks to several months) in which to obtain a desired population of germinants, which can then be outplanted within a narrow time frame (e.g. one day up to two weeks), or during a winter dormant period, thereby resulting in a synchronized population at outplanting. The ability to synchronize the production of germinants in preparation for transplantation is particularly useful in the context of planting clonal field tests.

The methods of the present invention can be used to store conifer somatic embryo germinants from any conifer species, such as members of the family Pinacea, including members of the genus *Pinus* (e.g., loblolly pine (*Pinus taeda*)), or such as members of the genus *Pseudotsuga* (e.g., Douglas-fir (*Pseudotsuga menziesii*)).

The germinants may be produced by any method that yields conifer somatic embryo germinants. For example, germinants may be produced by first culturing conifer somatic embryos by known protocols, such as the methods described in U.S. Pat. Nos. 6,134,830 and 5,563,061. After the embryos have reached a mature cotyledonary stage they are then placed on a germination medium under environmental conditions of 21° C. to 27° C. for a sufficient period of time for an epicotyl and radicle to develop. This time period may range between 4 and 14 weeks, depending on the particular species and genotype. More typically it is between 8 and 12 weeks. A suitable light/dark photoperiod may be used, such as a 24 hour photoperiod.

The germination medium typically has no exogenous hormones, a lowered nitrogen content and a reduced level of osmoticants. The germination medium typically contains agar and is sterilized prior to use. The germinants may be germinated under suitable conditions on solid germination media contained in any suitable container, such as in Petri dishes stored in germination boxes.

An example of a suitable germination medium for Douglas-fir (*Pseudotsuga menziesii*) is provided below in TABLE 1.

TABLE 1

| *Pseudotsuga menziesii* $BM_G$ Germination Media | |
|---|---|
| Constituent | Concentration, mg/L |
| $NH_4NO_3$ | 206.3 |
| $KNO_3$ | 1170.0 |
| $CaCl_2 \cdot 6H_2O$ | 220.0 |
| $KH_2PO_4$ | 85.0 |
| $MgSO_4 \cdot 7H_2O$ | 185.0 |
| $MnSO_4 \cdot H_2O$ | 8.45 |
| $ZnSO_4 \cdot 7H_2O$ | 4.30 |
| $CuSO_4 \cdot 5H_2O$ | 0.013 |
| $FeSO_4 \cdot 7H_2O$ | 13.93 |
| $Na_2EDTA$ | 18.63 |
| $H_3BO_3$ | 3.10 |
| $NaMoO_4 \cdot 2H_2O$ | 0.125 |
| $CoCl_2 6H_2O$ | 0.0125 |
| KI | 0.42 |
| myo-Inositol | 100.0 |
| Thiamine•HCL | 1.00 |
| Nicotinic acid | 0.50 |
| Pyridoxine•HCL | 0.50 |
| Glycine | 2.00 |
| L-Glutamine | 450.0 |
| Sugar | 20,000 |
| pH | 5.7 |
| Activated charcoal | 2500 |
| Tissue culture agar | 8000 |

In accordance with the methods of the invention, once developed, the germinants, while still on the sterile germination medium, are placed into a cold environment in which the temperature is in the range of about 0.5° C. to about 10° C., preferably from about 4° C. to about 8° C. Preferably the container comprising the germinants on the germination media is placed into the cold storage environment without any manipulation of the germinants required.

The germinants may be stored in the cold environment until transplantation into growth medium for at least two weeks up to about 6 months (such as from 1 week to 20 weeks, or more preferably from about 2 weeks to about 4 weeks) without loss of post-transplant vigor, as described in EXAMPLES 1 and 2.

After the desired time of storage on germination medium and prior to transplant, the germinants are removed from the germination medium and placed in deionized water in sealed dishes. In some embodiments of the method, the germinants are transferred under sterile conditions, such as under a laminar flow hood. In other embodiments of the method, the germinants are transferred under non-sterile conditions. The germinants are stored in water for a time greater than about 1 hour at a temperature below about 24° C. Preferred temperatures are below 10° C., such as from about 0.5° C. to about 5° C. Improved rates of post transplant survival have been found for germinants stored in water for a period greater than 1 hour to about three weeks, as described in EXAMPLE 2.

The germinants stored in accordance with the method of the invention are eventually transferred to growth medium for further growth which eventually may result in conifer trees. The growth medium may be any suitable medium, such as potting soil, or a mixture of peat, vermiculate and perlite. The potted germinants are typically grown in a greenhouse and maintained at 24° C. for a 16 hour light period and at 18° C. for an 8 hour dark period. The plants may be compared and rated for survival percentage as described in EXAMPLES 1 and 2.

In another aspect, the present invention provides methods of increasing the conversion percentage from somatic embryos to plants growing in growth medium. The method according to this aspect of the invention comprise the steps of: (a) culturing conifer somatic embryos on sterile germination medium for a sufficient period of time to produce germinants, said germinants comprising a visible, well-defined epicotyl and radicle; (b) placing the germinants while still on sterile germination medium into a cold environment in which the temperature is in the range of 0.5° C. to 10° C. for a time period up to 6 months; (c) placing the germinants in water for a time greater than about 1 hour at a temperature below about 24° C.; and (d) removing the germinants from the water and transplanting them into growth medium for further growth. The methods of this aspect of the invention can be used to increase the conversion percentage from somatic embryos to plants growing in growth medium for any conifer species, such as members of the family Pinacea, including members of the genus *Pinus* (e.g., loblolly pine (*Pinus taeda*)), or such as members of the genus *Pseudotsuga* (e.g., Douglas-fir (*Pseudotsuga menziesii*)).

In some embodiments, the germinants are stored on sterile germination media for a time period from about 1 week up to 6 months, such as from 2 weeks to 20 weeks, or more preferably from about 2 weeks to about 4 weeks. In some embodiments, the germinants that have been pre-stored on germination media and then stored in water for a time period from about 1 hour up to 2 weeks, such as from about 1 week to about 2 weeks, more preferably about 1 week.

The following examples merely illustrate the best mode now contemplated for practicing the invention, but should not be construed to limit the invention.

EXAMPLE 1

This Example describes the results of an experiment demonstrating that a two-step storage treatment on Douglas-fir germinants increases the sterile storage period without causing detrimental effects to greenhouse survival.

Methods and Materials:

Germinants from ten different genotypes of Douglas-fir somatic embryos were produced up to the development stage using the methods described in Gupta, U.S. Pat. No. 5,563,061 and Welty, U.S. Pat. No. 6,134,830. Following the development stage, the cotyledonary embryos were placed on an agar gelled sterile germination medium, BM6, in Petri dishes for 4-12 weeks under environmental conditions of 21° C. to 27° C. until good epicotyl development was apparent (e.g., an epicotyl stem length of about 10 mm or greater, such as at least from 10 mm to 20 mm, such as at least 12 mm, at least 15 mm or greater). BM6 medium is a basal medium lacking growth hormones which has been modified by reducing sucrose, myo-inositol and organic nitrogen.

Once good epicotyl development was apparent, the closed germination containers containing the germinants on sterile germination medium were moved directly into a cooler at a temperature of about 4° C. and stored in the dark for various amount of time up to 6 months. At various time points after storage on germination media, the germinants were removed from the germination media and placed into Petri dishes that were half-filled with Millipore or Nanopure water and then sealed with parafilm. The roots of the germinants were immersed in water while the shoots floated on the surface. The germinants in water were transferred to a cold environment at a temperature of about 4° C. for a period of time up to 4 weeks.

Although the germinants were stored under sterile conditions up to this point, it was determined that the transfer, under a laminar flow hood, from the germination media to the Petri dishes containing water could result in desiccation of the germinants. Consequently, the transfer from germination media to water storage was not made under sterile conditions.

Germinants from ten different genotypes of Douglas-fir were treated as follows. Group I control samples were germinated on sterile germination media, then removed from the germination media and transplanted immediately into potting media without a period of storage. Group II germinants were germinated on sterile germination media in germination boxes, and the germination boxes were then moved into a dark cooler at 4° C. for 1 week followed by one week in water storage. Group III germinants were germinated on sterile germination media in germination boxes, the boxes were moved into a dark cooler at 4° C. for 2 weeks, followed by one week in water storage. Upon removal from storage, the Petri dishes and boxes were inspected for signs of contamination. No contamination was found during the following experiments. The germinants were transplanted into potting media and the percent survival was measured at 8 weeks post transplant. The potting media consisted of equal parts of peat vermiculate and perlite. The percent survival of the germinants treated under the various conditions are shown below in TABLE 2.

TABLE 2

Douglas-fir Percent Survival Post-transplant

| Time held in storage | Douglas-fir Genotype (percent survival 8 weeks post-transplant) | | | | | | | | | | Treatment Average | Paired Test |
|---|---|---|---|---|---|---|---|---|---|---|---|---|
| | 7306 | 7435 | 3637 | 5022 | 5008 | 5010 | 5002 | 7667 | 663 | 7744 | | |
| Control (no storage) | 64.3 | 22.6 | 67.1 | 60.5 | 46.1 | 37.3 | 32.3 | 91.7 | 53.9 | 89.2 | 56.5 | 0.813 |
| 1 week on Germination media + 1 week in $H_2O$ | 63.5 | 13 | 51.4 | 67.2 | 41.1 | 40.5 | 48.1 | 100.0 | 51.6 | 90.5 | 56.7 | |
| 2 weeks on Germination media + 1 week in $H_2O$ | 72.6 | 21.7 | 59.3 | 72.3 | 48.6 | 39.4 | 36.3 | 96.3 | 38.8 | 88.0 | 57.3 | |

Results:

As shown above in TABLE 2, greenhouse survival post transplant for germinants stored on germination media followed with one week of storage in water was at least as good, and in some cases better than that observed for water storage alone.

Conclusion:

The method of long term storage (e.g., 2 to 4 weeks, and likely up to 6 months) of Douglas-fir germinants on germination media followed by short term storage (e.g., 1 to 2 weeks) in water results in improved survival rates for transplants and provides a convenient method by which to accumulate germinants prior to transplant. This method provides several advantages including increased survival post-transplant, convenient storage of large numbers of germinants, and a reduced risk of microbe contamination prior to transplantation.

EXAMPLE 2

This Example describes experiments that measure the post-transplant survival of various loblolly pine genotypes after storage of germinants in water for various lengths of time as compared to the post-transplant survival of germinants that were stored on germination media followed with one week of storage in water.

Methods and Materials:

Germinants Stored in Water

A control experiment was carried out to determine the effect of storage in water for various time periods on the post-transplant survival of loblolly pine clones. Germinants from tree different loblolly pine genotypes were produced up to the germination stage using the methods described in Gupta, U.S. Pat. No. 5,563,061 and Welty, U.S. Pat. No. 6,134,830. The germinants for each clone were removed from germination media and placed into Petri dishes that were half filled with Millipore or Nanopure water and then sealed with parafilm. The Petri dishes were stacked in a labeled crisper (1 genotype to crisper) and then put into a dark walk-in cooler (approximately 4° C.) for the length of time indicated below in TABLE 3 prior to transplant. A control batch of germinants from each clone was transplanted in potting medium immediately without storage in water. The potting medium consisted of equal parts of peat, vermiculite, and perlite. The potted germinants were held for further growth in a greenhouse maintained at 24° C. for a 16 hour light period and at 18° C. for an 8 hour dark period. After $ weeks or more the plants were rated for survival percentage. The results are shown below in TABLE 3.

Germinants Stored on Germination Media Followed by Short Term Storage in Water

Germinants from different loblolly pine genotypes were produced up to the germination stage using the methods described in Gupta, U.S. Pat. No. 5,563,061 and Welty, U.S. Pat. No. 6,134,830. The germinants from the different genotypes were stored on sterile germination media in the dark at 4° C. for various time periods, as shown in TABLE 4, then the germinants were removed from germination media and placed into Petri dishes that were half-filled with Millipore or Nanopure water and then sealed with parafilm and stored at 4° C. for a week prior to transplantation. The results are shown in TABLE 4 and TABLE 5.

TABLE 3

Loblolly Pine Survival Post-Transplant After Storage in Water

| Time in Water Storage | Loblolly Pine Genotype (percent survival 8 or more weeks post transplant) | | | | 3 Clone Average | 4 Clone Average | Pr > t Paired test (3 or 4 genotypes) |
|---|---|---|---|---|---|---|---|
| | 55 | 56 | 68 | 75 | | | |
| Control (not stored) | — | 99.1 | 96 | 88.6 | 94.6 | — | 0.966 |
| 1 week | — | 98.6 | 93.8 | 91.1 | 94.5 | — | |
| Control (not stored) | 94.4 | 99.1 | 96 | 86.5 | 93.9 | 94.0 | 0.164 |
| 2 weeks | 88.9 | 96.7 | 84.3 | 50.8 | 77.3 | 80.2 | |

TABLE 3-continued

Loblolly Pine Survival Post-Transplant After Storage in Water

| Time in Water Storage | Loblolly Pine Genotype (percent survival 8 or more weeks post transplant) | | | | 3 Clone Average | 4 Clone Average | Pr > t Paired test (3 or 4 genotypes) |
|---|---|---|---|---|---|---|---|
| | 55 | 56 | 68 | 75 | | | |
| Control (not stored) | — | 98.8 | 96 | 87 | 93.9 | — | 0.860 |
| 3 weeks | — | 96.9 | 96 | 89.7 | 94.2 | — | |
| Control (not stored) | 93.6 | 97.8 | 96.2 | 88.5 | 94.2 | 94.0 | 0.728 |
| 4 weeks | 95.7 | 96.5 | 98.0 | 83.3 | 92.6 | 93.4 | |
| Control (not stored) | — | 98.3 | 96 | 86.6 | 93.6 | — | 0.147 |
| 5 weeks | — | 96.9 | 84 | 71.9 | 84.3 | — | |

TABLE 4

Loblolly Pine Survival Post-transplant After Storage on Germination Media Followed by Storage in Water

| Time held in Storage | Loblolly Pine Genotype (percent survival 8 or more weeks post transplant) | | | 3-Clone Average | Pr > t Paired test |
|---|---|---|---|---|---|
| | 55 | 56 | 75 | | |
| Control = 0 days on germination media + 21 days in H$_2$O | 100 | 95.5 | 79.1 | 91.5 | — |
| 14 days on germination media + 7 days in H$_2$O | 100 | 93.4 | 77.6 | 90.3 | 0.195 |
| 21 days on germination media + 7 days in H$_2$O | 97.3 | 98.4 | 82.1 | 92.6 | 0.628 |
| Controls = 0 days on germination media + 21 days in H$_2$O | 100 | 100 | 94.6 | 98.2 | — |
| 28 days on germination media + 7 days in H$_2$O | 100 | 92.5 | 91.3 | 94.6 | 0.239 |

TABLE 5

Loblolly Pine Survival Post-transplant After Storage on Germination Media Followed by Storage in Water

| Time held in Storage | Loblolly Pine Genotype | | | | | | | | | | Treatment Average (10 genos) | Treatment Average (4 genos) |
|---|---|---|---|---|---|---|---|---|---|---|---|---|
| | 202 | 205 | 212 | 213 | 214 | 215 | 226 | 228 | 241 | 243 | | |
| Control- No Storage | 93.8 | 100 | 96.7 | 96.6 | 75 | 97.7 | 98 | 100 | 100 | 93.8 | 95.2 | 97.8 |
| 2 weeks on Germ media + 1 week in H$_2$O | — | — | 100 | 96.3 | — | — | 97.7 | 100 | — | — | | 98.5[1] |
| 4 weeks on Germ media + 1 week in H$_2$O | 89.3 | 100 | 95.9 | 98 | 89.8 | 100 | 93.6 | 98.1 | 93.3 | 96.3 | 95.4[2] | 96.4[3] |

[1]Paired t-test comparing 2-week Box Storage against the control (4 genos) (Pr > t) = 0.50
[2]Paired t-test comparing 4-week Box Storage against the control (10 genos) (Pr > t) = 0.89
[3]Paired t-test comparing 4-week Box Storage against the control (4 genos) (Pr > t) = 0.32

Results:

As shown above in TABLE 2, the results indicate that short term water storage (e.g., 1 week) increases the post-transplant survival of loblolly pine germinants, however longer term water storage (e.g., 2 to 4 weeks or longer) decreases the percent survival in the majority of clone genotypes (¾) tested.

As shown above in TABLE 3 and TABLE 4, longer term storage on germination media (e.g., from 2 to 4 weeks or longer) followed by short term (e.g., 1 week) water storage resulted in post-transplant survival of loblolly pine germinants at survival rates at least as good as, and in some cases better than, germinants that were planted directly into potting media with no storage.

Conclusion

The method of long term storage (e.g., 2 to 4 weeks up to 6 months) of loblolly pine germinants on germination media followed by short term storage (e.g., 1 to 2 weeks) in water results in improved survival rates for transplants and provides a convenient method by which to accumulate germinants prior to transplant.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of producing a synchronized population of conifer somatic embryo germinants in preparation for transplantation, comprising:
    (a) culturing conifer somatic embryos on sterile germination medium for a sufficient period of time to produce germinants comprising a visible, well-defined epicotyl stem of a desired length;
    (b) selecting a plurality of germinants having an epicotyl stem of the desired length;
    (c) storing the selected germinants having an epicotyl stem of the desired length produced in step (a) while still on the sterile germination medium from step (a) in a cold environment in which the temperature is in the range of 0.5° C. to 10° C. for a time period up to six months; and
    (d) transferring the germinants stored according to step (c) from the germination medium into water for a time of up to about four weeks at a temperature of about 0.5° C. to about 5° C. prior to planting the selected germinants into growth medium.

2. The method of claim 1, further comprising the step of planting the germinants in growth medium.

3. The method of claim 1, wherein the desired length is an epicotyl stem length of at least 10 mm.

4. The method of claim 2, wherein the germinants are planted in a clonal field test.

5. The method of claim 1, wherein the germinants are Douglas-fir.

6. The method of claim 1, wherein the germinants are loblolly pine.

7. The method of claim 1, wherein the desired length is an epicotyl stem length of about 10 mm to about 20 mm.

8. The method of claim 1, wherein the desired length is an epicotyl stem length of about 12 mm.

9. The method of claim 1, wherein the desired length is an epicotyl stem length of about 15 mm.

10. The method of claim 1, wherein the germinants are stored in water according to step (d) for a time of from about one week to about two weeks.

* * * * *